(12) United States Patent
Arhancet et al.

(10) Patent No.: US 9,410,036 B2
(45) Date of Patent: Aug. 9, 2016

(54) FUNCTIONALIZED POLYMER COMPOSITIONS

(71) Applicant: Novus International Inc., St. Charles, MO (US)

(72) Inventors: Graciela B. Arhancet, St. Charles, MO (US); Matthew Mahoney, St. Charles, MO (US); Xiaojun Wang, St. Charles, MO (US); Rangarani Karnati, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 0 days.

(21) Appl. No.: 15/047,669

(22) Filed: Feb. 19, 2016

(65) Prior Publication Data

US 2016/0185899 A1    Jun. 30, 2016

Related U.S. Application Data

(62) Division of application No. 13/763,135, filed on Feb. 8, 2013, now Pat. No. 9,284,294.

(60) Provisional application No. 61/596,843, filed on Feb. 9, 2012, provisional application No. 61/597,444, filed on Feb. 10, 2012.

(51) Int. Cl.
| | |
|---|---|
| *A61K 31/765* | (2006.01) |
| *A23D 9/013* | (2006.01) |
| *C07C 315/00* | (2006.01) |
| *C07C 27/04* | (2006.01) |
| *C08L 67/04* | (2006.01) |
| *C07D 319/12* | (2006.01) |

(52) U.S. Cl.
CPC ............... *C08L 67/04* (2013.01); *C07D 319/12* (2013.01)

(58) Field of Classification Search
None
See application file for complete search history.

*Primary Examiner* — Jeffrey T Palenik
(74) *Attorney, Agent, or Firm* — Polsinelli PC

(57) ABSTRACT

The invention relates to functionalized polymers including homopolymers and copolymers and their uses in industrial applications and in agricultural applications. In particular, the homopolymers and copolymers may be, for example, used in polymer blends, used as nutritives and in feed compositions, and used in combination with a pharmaceutical or nutritive.

17 Claims, 5 Drawing Sheets
(3 of 5 Drawing Sheet(s) Filed in Color)

FUNCTIONALIZED POLYMER COMPOSITIONS

CROSS-REFERENCE TO RELATED APPLICATIONS

This application is a divisional application of U.S. application Ser. No. 13/763,135, filed Feb. 8, 2013, which claims the priority of U.S. provisional application No. 61/596,843, filed Feb. 9, 2012, and U.S. provisional application No. 61/597,444, filed Feb. 10, 2012, each of which is hereby incorporated by reference in its entirety.

FIELD OF THE INVENTION

The invention relates to functionalized polymer compositions and their uses in industrial and agricultural applications.

BACKGROUND OF THE INVENTION

Polymers and polymeric compositions are useful compounds for a variety of purposes. Polymers of esters (polyesters) are of particular importance because of their biodegradability and potential for biocompatibility. While current polyester compounds find application in a variety of uses, many lack desired chemical functionalities.

In particular, heteroatom substituted polymer compounds are desirable as new polymers to exhibit enhanced chemical properties. However, attempts to polymerize heteroatom functionalities are often challenging synthetically and offer limited flexibility in the range of heteroatom groups that can be added.

Polymers of heterosubstituted monomers can also be useful for delivery of the monomers under certain conditions. The polymers may exhibit differential solubility and stability under different conditions which makes them particularly suitable for delivery of the monomeric units. For example, some nutrients are degraded substantially before the nutrient can reach the bloodstream. A number of strategies have been developed to improve the bioavailability of these nutrients. Polymers of the desired monomer nutrients may provide stability characteristics such that the nutrients can be delivered in a more efficient manner.

SUMMARY OF THE INVENTION

Among the various aspects of the present disclosure is the provision of a homopolymer. The homopolymer has an average molecular weight above 800 Da and comprises the repeat unit of Formula (I):

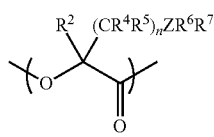

wherein,
$R^2$, $R^4$, and $R^5$ are independently chosen from hydrogen, hydrocarbyl, and substituted hydrocarbyl;
$R^6$ is chosen from hydrogen, hydrocarbyl, and substituted hydrocarbyl;
$R^7$ is optionally present, when present it is chosen from hydrogen, hydrocarbyl, and substituted hydrocarbyl;
Z is chosen from sulfur, sulfone, sulfoxide, and selenium; and
n is an integer $\geq 1$;
provided that where n is 2 and $R^6$ is methyl, then Z is other than sulfoxide.

In another embodiment, the present disclosure provides a copolymer having a repeat unit of comprising Formula (I) and at least one second repeat unit, provided that the second repeat unit is other than a repeat unit derived from an amino acid, the compound comprising Formula (I):

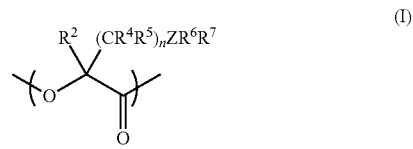

wherein,
$R^2$, $R^4$, and $R^5$ are independently chosen from hydrogen, hydrocarbyl, and substituted hydrocarbyl;
$R^6$ is chosen from hydrogen, hydrocarbyl, and substituted hydrocarbyl;
$R^7$ is optionally present, when present it is chosen from hydrogen, hydrocarbyl, and substituted hydrocarbyl;
Z is chosen from sulfur, sulfone, sulfoxide, and selenium; and
n is an integer $\geq 1$.

In still another embodiment, a process for forming a homopolymer or copolymer having an average molecular weight above about 800 Da is provided. The homopolymer or copolymer has a repeat unit comprising Formula (I), and the process comprises contacting monomers comprising Formula (V) under dehydration conditions with an acid catalyst to form the homopolymer or copolymer having the repeat unit of comprising Formula (I):

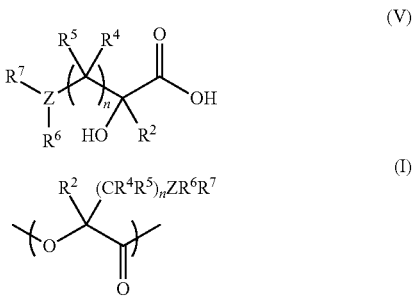

wherein,
$R^2$, $R^4$, and $R^5$ are independently chosen from hydrogen, hydrocarbyl, and substituted hydrocarbyl;
$R^6$ is chosen from hydrogen, hydrocarbyl, and substituted hydrocarbyl;
$R^7$ is optionally present, when present it is chosen from hydrogen, hydrocarbyl, and substituted hydrocarbyl;
Z is chosen from sulfur, sulfone, sulfoxide, and selenium; and
n is an integer $\geq 1$.

Other features and iterations of the invention are described in more detail below.

BRIEF DESCRIPTION OF DRAWINGS

The application file contains at least one photograph executed in color. Copies of this patent application and pub

DETAILED DESCRIPTION OF THE INVENTION

Figure 1:
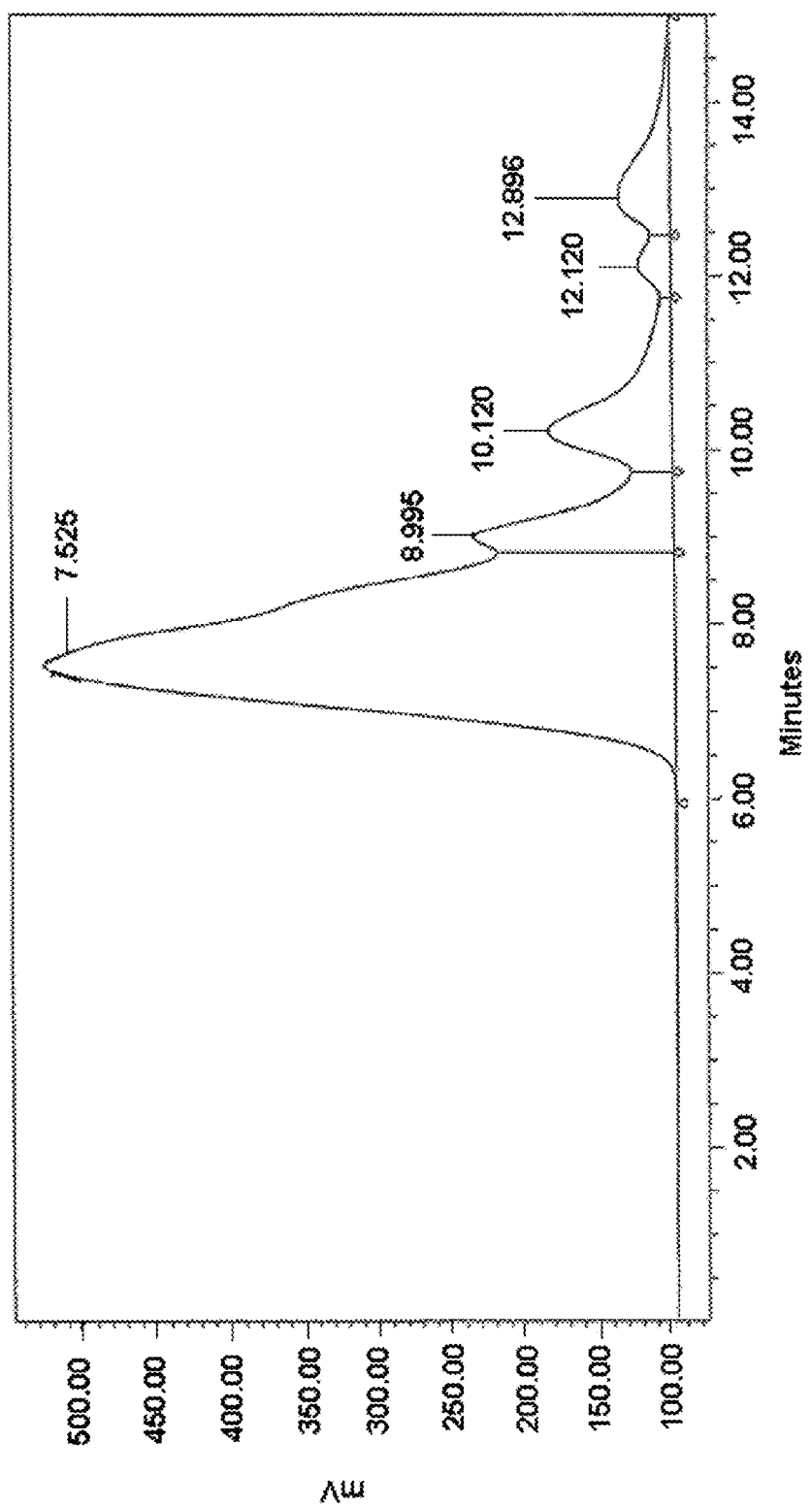
- FIG. 1 is a gel permeation chromatogram of polymer 1, a homopolymer of 2-hydroxy-4-(methylthio)-butanoic acid (HMTBA).

The present invention provides functionalized polymer compositions including homopolymers and copolymers having a repeat unit of Formula (I). Also provided are methods for making homopolymers and copolymers. The homopolymers and copolymers provided herein have advantageous physical properties which can, in some instances, provide a pH switch effect. The homopolymers and copolymers may be used in a variety of contexts including, but not limited to, in polymer blends, in animal feed, and in combination with a pharmaceutical agent.

(I) Homopolymers

In one aspect, the present invention provides a homopolymer, wherein the homopolymer has an average molecular weight above about 800 Da and comprises a repeat unit comprising Formula (I):

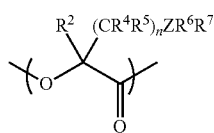

(I)

wherein,
$R^2$, $R^4$, and $R^5$ are independently chosen from hydrogen, hydrocarbyl, and substituted hydrocarbyl;
$R^6$ is chosen from hydrogen, hydrocarbyl, and substituted hydrocarbyl;
$R^7$ is optionally present, when present it is chosen from hydrogen, hydrocarbyl, and substituted hydrocarbyl;
Z is chosen from sulfur, sulfone, sulfoxide, and selenium; and
n is an integer $\geq 1$;
provided that where n is 2, and $R^6$ is methyl, Z is not sulfoxide.

In some embodiments, $R^2$ may be chosen from hydrocarbyl, substituted hydrocarbyl, and hydrogen. In certain embodiments, $R^2$ may be an alkyl group. Alkyl groups may include a lower chain alkyl groups such as, for example, methyl, ethyl, propyl, butyl, pentyl, and hexyl. In another embodiment, $R^2$ may be phenyl, benzyl, or substituted phenyl or benzyl. In preferred embodiments, $R^2$ may be hydrogen.

$R^4$ and $R^5$ are independently chosen from hydrocarbyl, substituted hydrocarbyl, and hydrogen. In one embodiment, $R^4$ and $R^5$ are both hydrogen. In another embodiment, one of $R^4$ and $R^5$ are hydrogen and the other is alkyl. The $—(CR^4R^5)_n—$ may constitute a hydrocarbyl chain that may be linear or branched, with n representing the number of linked carbon atoms in the chain. In various embodiments, n may be equal to or greater than 1. In some embodiments, n may range from 1 to 20 and the hydrocarbyl chain comprises from 1 to 20 linked carbon atoms, more preferably n may range from 1 to 5. In still another embodiment, n may be equal to 1, 2, 3, 4, 5, 6, 7, 8, 9, 10, 11, 12, 13, 14, 15, 16, 17, 18, 19, or 20. $R^4$ and $R^5$ may be hydrogen throughout the chain, in other aspects select $R^4$ and $R^5$ may be hydrocarbyl or substituted hydrocarbyl.

The repeat unit comprising Formula (I) also contains a heteroatom Z group. In some embodiments, the Z group may be selenium or a sulfur atom, including thiol, sulfoxide, and sulfone groups. The selenium or sulfur atoms may be charged and/or be present in various oxidation states within the molecule. Where the Z carries a charge, the composition may further comprise a counterion including, but not limited to, lithium, sodium, potassium, calcium, magnesium, and the like. In one embodiment, where n is two and $R^6$ is methyl, Z is not sulfoxide.

$R^6$ in the repeat unit may be chosen from hydrogen, hydrocarbyl, and substituted hydrocarbyl. Where $R^6$ is a hydrocarbyl, it may be an alkyl group. In some embodiments, $R^6$ is preferably a lower chain alkyl group such as methyl, ethyl, propyl, butyl, pentyl, or hexyl. The lower alkyl groups may additionally be branched or cyclic. Non-limiting examples include isopropyl, isobutyl, sec-butyl, t-butyl, cyclopropyl, cyclobutyl, cyclopentyl, and the like. In another embodiment, $R^6$ may be phenyl, benzyl, or substituted phenyl or benzyl. In an exemplary embodiment, $R^6$ may be methyl.

$R^7$ may be optionally present in the repeat unit comprising Formula (I). When present, $R^7$ is chosen from hydrocarbyl, substituted hydrocarbyl, and hydrogen. Where $R^7$ is a hydrocarbyl, it may be any alkyl group, but is preferably a lower chain alkyl group such as methyl, ethyl, propyl, butyl, pentyl, or hexyl. The lower alkyl groups may additionally be branched or cyclic. Non-limiting examples include isopropyl, isobutyl, sec-butyl, t-butyl, cyclopropyl, cyclobutyl, cyclopentyl, and the like. In another embodiment, $R^7$ may be phenyl, benzyl, or substituted phenyl or benzyl. In a further embodiment, $R^7$ may be hydrogen.

The average molecular weight of the homopolymer may be above 800 Da. In one embodiment, the molecular weight ranges from about 800 Da to about 2000 Da or from about 800 Da to about 1200 Da or from about 1200 Da to about 2000 Da. In an alternative embodiment, the average molecular weight ranges from about 1000 Da to about 2000 Da. In further alternative embodiments, the molecular weight of the homopolymer may range from about 800 Da to about 3000 Da, or from about 800 Da to about 4000 Da, or from about 800 Da to about 5000 Da, or from about 800 Da to about 10,000 Da.

In still another embodiment, the homopolymer may have an average molecular weight that ranges from about 2,000 to about 5,000 Da, from about 2,000 to about 10,000 Da, from about 2,000 to about 30,000, from about 2,000 to about 50,000 Da. In still other embodiments, the molecular weight may range from about 5,000 to about 10,000 Da, from about 10,000 to about 20,000, from about 20,000 to about 30,000

Da, from about 30,000 to about 40,000 Da, from about 40,000 Da to about 50,000 Da. The average molecular weight may be determined by gel permeation chromatography.

The homopolymers disclosed herein generally have a narrow molar mass distribution. The polydispersity index (PDI=Mw/Mn) is generally less than about 1.8. In some embodiments, the PDI is less than about 1.7, less than about 1.6, less than about 1.5, less than about 1.4, less than about 1.3, less than about 1.2, or less than about 1.1.

In one preferred embodiment, the homopolymer comprises a repeat unit comprising Formula (II):

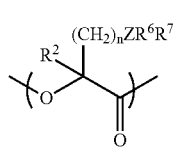

(II)

wherein, $R^2$, $R^6$, $R^7$, Z, and n are as defined for Formula (I).

In another exemplary embodiment, the homopolymer comprises a repeat unit comprising Formula (III):

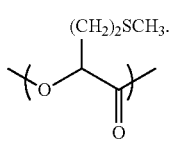

(III)

In some aspects of the invention, the repeat units of the homopolymers have chiral centers. As one example, the carbon alpha to the carbonyl in the compound of Formula (I), (II), or (III) may be chiral and may have an R or an S configuration. In some embodiments, the configuration at this position may be R. In other embodiments, the configuration at this position may be S. In various aspects, the repeat units may be all R, all S, or comprise a combination of R and S repeat units, for example, the configuration of the repeat units may alternate in block or randomly.

The homopolymers disclosed herein may be linear, coiled, ring, or branched polymers. Branched homopolymers include, without limit, star polymers, comb polymers, brush polymers, dendrimers, dendronized polymers, and ladder polymers. The homopolymers may be crystalline or semi-crystalline.

The homopolymers may be terminated by groups including carboxylic acid and hydroxyl. In some embodiments, the homopolymers can be modified such that they are terminated on each end independently by any group including hydrogen, hydrocarbyl, and substituted hydrocarbyl. In other embodiments, the homopolymers are terminated by groups independently chosen from alkyl, alkenyl, aryl, substituted alkyl, substituted alkenyl, substituted aryl. In preferred embodiments, the homopolymers are terminated by a hydroxyl group on both ends.

The homopolymers disclosed herein may be substantially free of monomers. In some embodiments, the percentage of free monomer may vary from about 0% to about 5% of the total composition. In other embodiments, the percent of free monomer may be less than about 5% or less than about 3% or less than about 2%, or less than about 1%, or less than about 0.5%.

The compounds or compositions comprising the compounds provided herein may have one set of properties under one set of conditions and different properties under different conditions. In some embodiments, the compounds provided herein may be stable under approximately neutral pH. In other embodiments, the compounds provided herein may substantially hydrolyze in aqueous solutions at pH values of less than about 6.0, less than about 5.0, less than about 3.0, less than about 2.0, or less than about 1.0.

A stable composition as used herein means that the homopolymers are substantially unhydrolyzed. "Substantially unhydrolyzed" may describe a composition where less than 25% of the homopolymer is hydrolyzed to a monomer, dimer or trimer. In some aspects, a substantially unhydrolyzed homopolymer may be less than about 15% free monomer, or less than 10% free monomer, or more preferably, less than about 9%, 8%, 7%, 6%, 5%, 4%, 2%, or more preferably, less than about 1% free monomer to the total homopolymer. "Neutral conditions", as described herein, generally refer to a pH ranging from about 6 to about 7.5.

The homopolymers may be substantially hydrolyzed under acidic or basic conditions. For example, the homopolymers may hydrolyze in an aqueous solution having a pH of about 5, 4.5, 4, 3.5, 3, 2.5, 2, 1.5, 1, or 0.5, or any pH including and between the two values to give a substantially hydrolyzed composition. A "substantially hydrolyzed" composition, as used herein, refers to a solution where greater than about 30% of the composition is a free monomer, dimer, or trimer. In some aspects, a substantially hydrolyzed composition may be about 50% free monomer, or 60% free monomer, or greater. In another aspect, a substantially hydrolyzed composition may have a free monomer content of about 80% or greater. Hydrolysis under particular conditions produces a pH switch effect for the compositions.

The homopolymers as described in this section may be further processed as a melt, an extrudate, a film, or a coating. A melt composition is a polymer or a composition comprising a polymer above its melting point such that it is in its molten liquid state, that is, at a temperature above the melting point of the composition. A melt composition may have advantageous chemical or physical properties, and may be formed or subjected to further processing in its molten state. In another aspect, the homopolymers may be extruded to give particular properties. Generally, processes of extrusion involve feeding the composition into an extruder which heats and shears the mixture. Shearing may occur through an apparatus that pushes the heated composition through an orifice. The extruder may be chosen from any commercially available extruder and may be a single screw extruder, or, preferably a twin-screw extruder that mechanically shears the mixture with the screw elements.

The homopolymers described in this section may be useful in a variety of contexts including as polymer blends (for example, as plasticizers and in thin films) as described in section (IV), as a feed composition (for example as a nutritive or in a feed composition or feed premix) as described in section (V), in combination with nutritives or pharmaceuticals (as described in section VI). The homopolymers may further be utilized as antimicrobials, anticorrosives, or antioxidants, surfactants, plasticizers, coatings, and dispersants.

(II) Copolymers

In another aspect, the disclosure provides a copolymer. The copolymer comprises a first repeat unit comprising Formula (I). The repeat unit comprising Formula (I) is as described in section (I), with the exception that where n is two and $R^6$ is methyl, then Z may be sulfoxide. The copolymer further comprises at least one second repeat unit, where the second repeat unit is other than a repeat unit derived from an amino acid. The copolymer has an average molecular weight above about 800 Da.

In some embodiments, the second repeat unit comprises Formula (I), provided however, that the second repeat unit is substituted differently in at least one position than the first repeat unit.

In another embodiment, the second repeat unit may be chosen from any known to those of skill in the art. Non-limiting examples include acrylate, an aminoacrylate, an alkylene succinate, an alkylene oxalate, an anhydride, an arylate, a carbonate, a cellulose, a caprolactone, a cyanoacrylate, a cyclic ether, a dihydropyran, a dioxane, a dioxanone, an ether ether ketone, an ethylene glycol, an ester, a fumarate, an hydroxyl alkanoate, an hydroxy ester, an imide, a ketal, a lactide, lactone, a terephthalate, a tetrahydrofuran, a trimethylene carbonate, an urethane, or a derivative of any of the forgoing, or mixtures thereof. In a preferred embodiment, second repeat unit is chosen from lactide or valeric acid.

"Derived from an amino acid" as used herein, refers to a repeat unit of the general formula (NHCRCO), wherein R is hydrocarbyl, substituted hydrocarbyl, or hydrogen.

The weight ratio of the first repeat unit to the second repeat unit may vary depending on the desired properties of the copolymer. In some aspects, the weight ratio of the first repeat unit comprising Formula (I) to the second repeat unit may range from about 99.9:0.1 to about 0.1:99.9. In various embodiments the weight ratio of the first repeat unit comprising Formula (I) to the second repeat unit may be about 99:1, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, 5:95, or 1:99 weight %. Similarly, in embodiments in which the combination comprises three or more repeat units, the amount of each compound can and will vary.

The copolymers disclosed herein may be may be alternating copolymers, periodic copolymers, random copolymers, block copolymers, or graft copolymers. The copolymers may also be linear, coiled, ring, or branched polymers. Suitable branched copolymers include star polymers, $AB_2$ star polymers, palm-tree $AB_n$ polymers, H-shaped $B_2AB_2$ polymers, dumbbell polymers, star block $AB_n$ polymers, star $A_nB_n$ polymers, comb polymers, brush polymers, dendrimers, dendronized polymers, ladder polymers, and so forth. The copolymers may be crystalline or semi-crystalline.

The copolymers may be terminated on each side independently by any group including hydrogen, hydrocarbyl, and substituted hydrocarbyl. In other embodiments, the copolymers are terminated by groups independently chosen from alkyl, alkenyl, aryl, substituted alkyl, substituted alkenyl, substituted aryl.

The average molecular weight of the copolymer may be above 800 Da. In one embodiment, the molecular weight ranges from about 800 Da to about 2000 Da or from about 800 Da to about 1200 Da or from about 1200 Da to about 2000 Da. In an alternative embodiment, the average molecular weight ranges from about 1000 Da to about 2000 Da. In other alternative embodiments, the molecular weight of the copolymer may range from about 800 Da to about 3000 Da, or from about 800 Da to about 4000 Da, or from about 800 Da to about 5000 Da, or from about 800 Da to about 10,000 Da.

In still other embodiments, the copolymer may have an average molecular weight that ranges from about 2,000 to about 5,000 Da, from about 2,000 to about 10,000 Da, from about 2,000 to about 30,000, from about 2,000 to about 50,000 Da. In still other embodiments, the molecular weight may range from about 5,000 to about 10,000 Da, from about 10,000 to about 20,000, from about 20,000 to about 30,000 Da, from about 30,000 to about 40,000 Da, from about 40,000 Da to about 50,000 Da. The average molecular weight may be determined by gel permeation chromatography.

The copolymers disclosed herein generally have a narrow molar mass distribution. The polydispersity index (PDI=Mw/Mn) is generally less than about 1.8. In some embodiments, the PDI is less than about 1.7, less than about 1.6, less than about 1.5, less than about 1.4, less than about 1.3, less than about 1.2, or less than about 1.1.

The copolymers may also be characterized by a low percentage of free monomers as described for homopolymers in section (I). In some embodiments, the percent free monomer may be less than about 5%, less than about 4%, less than about 3%, less than about 2%, less than about 1%, or less than about 0.5% to the amount of copolymer.

In some aspects of the invention, the repeat units of the copolymers may have chiral centers. As one example, the carbon alpha to the carbonyl in the compound of Formula (I) may be chiral and may have an R or an S configuration. In some embodiments, the configuration at this position may be R. In other embodiments, the configuration at this position may be S. In various aspects, the repeat units may be all R, all S, or comprise a combination of R and S repeat units, for example, the repeat units may alternate in block or randomly. The second repeat units may be chiral or achiral. When chiral, they may have an R or an S configuration. In some embodiments, the configuration at this position may be all R all S or a mixture of R and S.

The copolymers may have one set of properties under one set of conditions and different properties under different conditions. In some embodiments, the copolymers provided herein may be stable under approximately neutral pH. In other embodiments, the copolymers provided in this section may substantially hydrolyze in aqueous solutions at pH values of less than about 6.0, less than about 5.0, less than about 3.0, less than about 2.0, or less than about 1.0.

The copolymers as described in this section may be further processed as a melt, an extrudate, a film, or a coating. A melt composition is a polymer or a composition comprising a polymer above its melting point such that it is in its molten liquid state, that is, at a temperature above the melting point of the composition. A melt composition may have advantageous chemical or physical properties, and may be formed or subjected to further processing in its molten state. In another aspect, the copolymers may be extruded to give particular properties. Generally, processes of extrusion involve feeding the composition into an extruder which heats and shears the mixture. Shearing may occur through an apparatus which pushes the heated composition through an orifice. The extruder may be chosen from any commercially available extruder and may be a single screw extruder, or, preferably a twin-screw extruder that mechanically shears the mixture with the screw elements.

The copolymers described in this section may be useful in a variety of contexts including as polymer blends (for example, as plasticizers and in thin films) as described in section (IV), as a feed composition (for example as a nutritive or in a feed composition or feed premix) as described in section (V), in combination with nutritives or pharmaceuticals (as described in section VI). The copolymers may further be utilized as antimicrobials, anticorrosives, antioxidants, coatings, adhesives, binders, plasticizers, and dispersants.

(III) Processes of Making

Another aspect of the disclosure provides a process for forming a homopolymer or a copolymer having an average molecular weight above about 800 Da and a repeat unit comprising Formula (I), the process comprising contacting monomers comprising Formula (V):

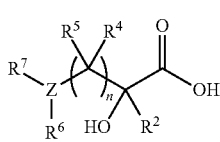
(V)

under dehydration conditions with an acid catalyst to form the homopolymer or copolymer having the repeat unit comprising Formula (I):

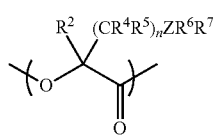
(I)

wherein,
$R^2$, $R^4$, and $R^5$ are independently chosen from hydrogen, hydrocarbyl, and substituted hydrocarbyl;
$R^6$ is chosen from hydrogen, hydrocarbyl, and substituted hydrocarbyl;
$R^7$ is optionally present, when present it is chosen from hydrogen, hydrocarbyl, and substituted hydrocarbyl;
Z is chosen from sulfur, sulfone, sulfoxide, and selenium; and
n is an integer $\geq 1$.

Generally, the reaction involves three steps. The first step (Step A) involves forming a reaction mixture comprising monomers and subjecting the reaction mixture to dehydration conditions. The second step (Step B) involves adding a catalyst to the reaction mixture and subjecting the mixture to reduced pressure. The third step (Step C) involves reducing the pressure and raising the temperature of the reaction mixture to give the homopolymers and copolymers.

(a). Step A

Step A of the process involves forming a reaction mixture comprising a plurality of monomers and subjecting the reaction mixture to dehydration conditions. In some aspects, the monomers comprise Formula (V):

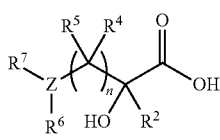
(V)

wherein,
$R^2$, $R^4$, and $R^5$ are independently chosen from hydrogen, hydrocarbyl, and substituted hydrocarbyl;
$R^6$ is chosen from hydrogen, hydrocarbyl, and substituted hydrocarbyl;
$R^7$ is optionally present, when present it is chosen from hydrogen, hydrocarbyl, and substituted hydrocarbyl;
Z is chosen from sulfur, sulfone, sulfoxide, and selenium; and
n is an integer $\geq 1$.

In another embodiment, the monomers comprise Formula (Va):

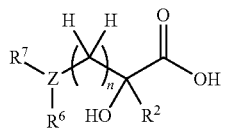
(Va)

wherein, $R^2$, $R^6$, $R^7$, Z, and n are as defined for Formula (V).

In an exemplary embodiment, the monomers comprise Formula (Vb):

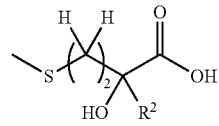
(Vb)

wherein, $R^2$ is as defined in for Formula (V).

In some embodiments, the monomers are provided to the contacting step with a low water concentration. For example, the starting materials may be provided to Step A with a water content below about 5%, below about 3%, below about 2%, or below about 1%.

(i). Additional Monomer

In one embodiment, the process produces a copolymer. In such embodiments, the reaction mixture comprises a monomer compound comprising Formula (V) and at least one additional monomer. In one embodiment, the additional monomer is also compound comprising Formula (V), provided that the substitution is different from the first in at least one respect.

In another embodiment, the additional monomer forms the copolymer unit that is chosen from diacid, diols, hydroxyl acid, acrylate, an aminoacrylate, an alkylene succinate, an alkylene oxalate, an anhydride, an arylate, a carbonate, a cellulose, a caprolactone, a cyanoacrylate, a cyclic ether, a dihydropyran, a dioxane, a dioxanone, an ether ether ketone, an ethylene glycol, an ester, a fumarate, an hydroxyl alkanoate, an hydroxy ester, an imide, a ketal, a lactide, lactone, a methacrylate, a methyl olefin, an orthoester, a phosphazine, a styrene, a terephthalate, a tetrahydrofuran, a trimethylene carbonate, an urethane, a vinyl acetate, a vinyl ketone, a vinyl halide, a derivative of any of the forgoing, or mixtures thereof.

The ratio of the additional monomer to the compound comprising Formula (V) may range from about 99.9:0.1 to about 0.1:99.9 weight %. For example, the additional monomer may be provided in a ratio of 99:1, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, 5:95, or 1:99 weight % to the compound comprising Formula (V). Similarly, in embodiments in which the combination comprises three or more total monomers, the amount of each monomer can and will vary. In some exemplary embodiments, the additional monomer may be added in about a 50:50 weight % to the compound comprising Formula (V). In another embodiment, the additional monomer may be added in about a 75:25 weight % to the compound comprising Formula (V).

(ii). Solvent

Step A may be carried out in the presence of a solvent chosen from organic solvents and mixtures of organic solvent. The organic solvent may be a nonpolar solvent, a protic polar solvent, an aprotic polar solvent, or a combination thereof. Non-limiting examples of suitable nonpolar solvents include anisole, benzene, butyl acetate, tert-butyl methyl ether, chlorobenzene, chloroform, chloromethane, cyclohexane, dichloromethane, dichloroethane, di-tert-butyl ether, dimethyl ether, diethylene glycol, diethyl ether, diglyme, diisopropyl ether, ethyl tert-butyl ether, ethylene oxide, fluorobenzene, heptane, hexane, methyl tert-butyl ether, toluene, xylene and combinations thereof. Examples of suitable protic polar solvents include without limit water, alcohols (e.g., methanol, ethanol, isopropanol, n-propanol, isobutanol, n-butanol, s-butanol, t-butanol), diols (e.g., propylene glycol and the like), organic acids (e.g., formic acid, acetic acid, and so forth), amides (e.g., formamide, acetamide, and the like), and combinations of any of the above. Non-limiting examples of suitable aprotic polar solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), N-methyl-2-pyrrolidinone (NMP), 1,4-dioxane, ethyl acetate, ethyl formate, formamide, hexachloroacetone, hexamethylphosphoramide, methyl acetate, N-methylacetamide, methylethyl ketone, methylisobutyl ketone, N-methylformamide, methylene chloride, methoxyethane, morpholine, nitrobenzene, nitromethane, propionitrile, propyl acetates, sulfolane, tetramethylurea, tetrahydrofuran (THF), 2-methyl tetrahydrofuran, tetrahydropyran, trichloromethane, and combinations thereof. In another embodiment, the solvent may be an azeotropic distillation solvent. In a preferred embodiment, the solvent may be chosen from anisole, toluene, or xylene.

The weight-to-weight ratio of the solvent to the compound comprising Formula (V) can and will vary. Typically, the weight-to-weight ratio of the solvent to the compound comprising Formula (V) may range from about 1:1 to about 20:1. In various embodiments, the weight-to-weight ratio of the solvent to the compound comprising Formula (V) may be about 2:1, 3:1, 3.5:1, 4.0:1, 4.5:1, 5.0:1, 5.5:1, 6.0:1, 6.5:1, 7.0:1, 7.5:1, 8:1, or 10:1.

(iii). Reaction Conditions

Step A is generally conducted under dehydration conditions to promote formation of the homopolymer or copolymer. In certain embodiments, dehydration may be accomplished via distillation. For example, the reaction may be subjected to simple distillation, fractional distillation, azeotropic distillation, azeotropic distillation using a Dean Stark or another similar trap, steam distillation, vacuum distillation, distillation using a Dean Stark trap or another similar trap, and the like. In a preferred embodiment, Step A comprises azeotropic distillation.

Step A of the process may be conducted at a temperature that may range from about 100° C. to about 200° C. In some aspects, Step A may be conducted at a temperature of 100° C., 110° C., 120° C., 130° C., 140° C., 150° C., 160° C., 170° C., 180° C., 190° C., 200° C., or at a range between and including any two of these values. In a preferred embodiment, the temperature may be maintained at about 120° C. to about 150° C. throughout Step A. In general, Step A of the process is conducted at atmospheric pressure. In one embodiment, Step A of the process may be conducted under an inert atmosphere, such in an atmosphere of argon or nitrogen.

The duration of Step A can and will vary. In general, Step A may be allowed to proceed from about 2 hours to about 10 hours, or more preferably from about 4 hours to about 5 hours. In some aspects, the progress of the reaction may be monitored by measuring the amount of water removed in the process.

(b). Step B

Step B of the process comprises adding a catalyst to the reaction mixture and subjecting the mixture to reduced pressure.

The catalyst used in Step B can and will vary and may be chosen from catalysts known in the art. In some embodiments, the catalyst may be an acid catalyst chosen from organic acids, inorganic acids, and solid resins. Exemplary acid catalysts include, without limitation, boric acid, hydrochloric acid, trifluoroacetic acid, methanesulfonic acid, ortho- meta- and para-toluenesulfonic acid, sulfuric acid, phosphoric acid, tosylic acid, xylenesulfonic acid, Dowex resins, Amberlyst resins, Zn dust, and Sn based catalysts (such as, for example, Sn dust, tin oxide, tin (II) chloride, dibutyltin dilaurate, and stannous octoate), germanium dioxide, antimony trioxide, zinc oxide, iron (III) oxide, aluminum oxide, silicon dioxide, titanium dioxide, mixtures, and combinations thereof. In a preferred embodiment, the catalyst may be stannous octoate.

The acid catalyst may be added in a range of ratios to the compound comprising Formula (V). In some aspects the amount of catalyst added may range from about 0.01 wt % to about 1 wt % or higher of the compound comprising Formula (V). In some embodiments, the acid catalyst may be added in an amount ranging from about 0.1 wt % to about 0.5 wt % of the compound comprising Formula (V). In still other embodiments, the acid catalyst is added in an amount of about 0.1 wt %, 0.2 wt %, 0.3 wt %, 0.4 wt %, or 0.5 wt % the compound comprising Formula (V).

Step B further comprises a reduction of pressure. In a preferred embodiment, the pressure may be reduced to a pressure of about 100 mmHg to about 300 mmHg. In another aspect, the pressure may be reduced to about 200 mmHg. In some embodiments, the reduction of pressure occurs simultaneously with dehydration which may be accomplished as described in Step A. In a preferred embodiment, Step B comprises reduction of pressure with distillation.

In general, Step B may be conducted in a solvent as described in section (III)(a)(ii).

In some embodiments, the temperature of Step B may be approximately the same as the temperature of Step A. In another embodiment, the temperature of Step B may be higher than Step A. In various embodiments, Step B may be carried out at a temperature ranging from about 110° C. to about 210° C. In another embodiment, the reaction may be conducted at a temperature of about 110° C., 120° C., 130° C., 140° C., 150° C., 160° C., 170° C., 180° C., 190° C., 200° C., 210° C., or at a range between and including any two of these values. In one preferred embodiment, the temperature may be about 150° C.

The duration of Step B can and will vary. In general, the reaction may be allowed to proceed from about 2 hours to about 10 hours, or more preferably from about 3 hours to about 4 hours.

In some embodiments, a chain extender may be added to the reaction mixture. Chain extenders may be chosen from those known in the art. Suitable chain extenders include, without limitation, adipic acid, succinic acid, citric acid, isocyanates, such as 1,6-hexamethylene diisocyanate, oxazoline extenders, such as 2,2-bis(2-oxazoline) succinic anhydride and polyethene glycols (PEG).

Chain extenders may be provided in any amount in with respect to the compound comprising (V). In some embodiments, the chain extender is added in an amount ranging from about 0.01 wt % to about 10 wt % to the compounds comprising Formula (V).

(c). Step C

Step C of the process comprises an increase in temperature and a reduction in pressure.

In various embodiments, Step C may be carried out at a temperature ranging from about 140° C. to about 250° C. In another embodiment, the reaction may be conducted at a temperature of about 140° C., 150° C., 160° C., 170° C., 180° C., 190° C., 200° C., 210° C., 220° C., 230° C., 240° C., 250° C., or at a range between and including any two of these values. In a preferred embodiment, the temperature may be about 170° C. In some embodiments, temperature of Step C may be higher than the temperature of Step B.

Typically, Step C is conducted under reduced pressure. The degree to which the pressure is reduced in Step C varies with different embodiments. In some embodiments, the pressure may be maintained near the pressures of Step B and may range from about 100 mmHg to about 300 mmHg (1 mmHg=1 Torr=1000 mTorr) (Ambient=760 mmHg or Torr). In other embodiments, the pressure may be reduced to 0 mmHg to about 50 mmHg. In still another embodiment, the pressure may be reduced to about 0 mmHg, 10 mmHg, 20 mmHg, 30 mmHg, 40 mmHg, or 50 mmHg. In a preferred embodiment, the pressure may be reduced to about 30 mmHg. In some embodiments, Step C is conducted under dehydration conditions as described in Step A, and with a solvent as described in section (III)(a)(ii).

The duration of Step C can and will vary. In general, the reaction may be allowed to proceed from about 2 hours to about 10 hours, or more preferably from about 3 hours to about 4 hours. Typically, however, the reaction is allowed to proceed for a sufficient period of time until the reaction is complete, as determined by means well known to those of skill in the art. In this context, a "completed reaction" generally means that the final reaction mixture contains a significantly diminished amount the compounds comprising Formula (V) and a significantly increased amount of the homopolymer or copolymer compared to the amounts of each present at the beginning of the reaction. In some aspects, the reaction completeness can be measured by monitoring the amount of water removed in the process and comparing to the theoretical amount of water.

The yield of the homopolymer or copolymer produced by the method disclosed herein may be least about 30%, at least about 40%, at least about 50%, at least about 60%, at least about 70%, at least about 80%, or at least about 90%. In some embodiments, the resulting homopolymer or copolymer may have a low content of free monomers or dimers. The percentage of free monomer and dimer may range from about 0% to about 40% of the total homopolymer or copolymer produced. In some embodiments, the free monomer and dimer may comprise less than 30% of the total composition, or less than 20% of the total composition, or less than 10% of the total composition. In some embodiments, the percent free monomer may be less than about 10%, less than about 9%, less than about 8%, less than about 7%, less than about 6%, less than about 5%, less than about 4%, less than about 3%, less than about 2%, or less than about 1%.

The homopolymer or copolymers may be used as they are produced or optionally purified by means including by size exclusion chromatography (SEC), High Performance Liquid Chromatography (HPLC), ion-exchange chromatography, other types of chromatography, precipitation, or crystallization.

(IV) Polymer Blends

In an additional aspect, the invention encompasses a homopolymer or copolymer as described in section (I) or (II) and at least one additional polymer or copolymer to form a polymer blend. As used herein, a blend is a macroscopic homogeneous or miscible mixture of two or more different polymers and is formed by tailoring compositions to meet specific end-use requirements.

(a). Plasticizers and Elastomers

The homopolymers and copolymers described in sections (I) and (II) may be suitable as a plasticizer or an elastomer for blending with another polymer. The homopolymers and copolymers may lower the glass transition of the polymer(s) that they are blended with. When used as a plasticizer or elastomer, the compositions described in sections (I) and (II) may provide advantageous physical properties to another polymer. These physical properties include, but are not limited to, increases in plasticity, elasticity, flowablilty, durability, and flexibility.

In various embodiments, the additional polymer may be selected from crystalline and semicrystalline polymers. Examples include, without limitation, polymers of acrylates, aminoacrylates, alkylene succinates, alkylene oxalates, amides, amino acids, anhydrides, arylates, carbonates, cellulose, caprolactone, cyanoacrylates, dihydropyrans, dioxanes, dioxanones, ether ether ketones, ethylene glycol, fumarates, hydroxyalkanoates, hydroxyl-esters, imides, ketals, lactides, methacrylates, methyl olefins, orthoesters, phosphazines, styrenes, terephthalates, trimethylene carbonate, urathanes, vinyl acetates, vinyl ketones, vinyl halides, derivatives, isomers, and mixtures thereof. In preferred embodiments, the second polymer may be chosen from poly(lactide), poly (ethyl cellulose), and polyvinyl alcohol.

The additional polymer may vary in molecular weight. In some embodiments, the additional polymer may range from about 500 Da to greater than 100,000 Da. In some embodiments, the mass average molecular weight of the additional polymer may be about 10,000, 20,000 Da, 30,000 Da, 40,000 Da, 50,000 Da, 60,000 Da, 70,000 Da, 80,000 Da, 90,000 Da, 100,000 Da, and may range between and including any two of these values.

The amount of the homopolymer and copolymer to the additional polymer may depend on the desired properties of the combination. In some aspects, the weight ratio of the homopolymer or copolymer to the additional polymer may range from about 99.9:0.1 to about 0.1:99.9 weight %. In various embodiments the weight ratio of the homopolymer or copolymer to the additional polymer may be about 99:1, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, 5:95, or 1:99 weight %. In some embodiments, the blend comprises more than one additional polymer. In embodiments in which the combination comprises two or more additional polymers, the amount of each polymer can and will vary. In some embodiments, the homopolymer or copolymer as described in sections (I) or (II) may range from about 5% to about 30% by weight of the total composition.

In some aspects, the composition comprising the blend of polymers may comprise a melt, an extrudate, as described in section (I).

In one preferred embodiment, the blend is created with a compound comprising Formula (III) and another polymer.

Preferred polymers for creating a blend with Formula (III) are polymers and copolymers of lactide, glycolide, and ethylene glycol.

(b). Thin Films

In another embodiment, the blends described in this section are used as films. These films are characterized by a thin polymer layer, and may have advantageous properties such as biodegradability and biocompatibility, which may be linked to the pH switch aspects of the homopolymers and copolymers described in sections (I) and (II). The films may additionally have characteristics of strength, stretch, and transparency. In one embodiment, the thin film is a blend of a homopolymer, as described in section (I) and an additional polymer. In another embodiment, the thin film is a blend of a copolymer as described in section (II) and an additional polymer. In a particularly preferred embodiment, homopolymer or copolymer comprises a repeat unit of Formula (III).

The additional polymer may be as described in section (IV)(a). In a preferred embodiment, the additional polymer is poly(lactic) acid. The poly(lactic) acid used in the composition may have a molecular weight ranging from about 10 KDa to about 100 KDa. In various embodiments, the molecular weight of the poly(lactic) acid may be about 10 KDa, 20 KDa, 30 KDa, 40 KDa, 50 KDa, 60 KDa, 70 KDa, 80 KDa, 90 KDa, or 100 KDa.

A thin film may be made by solution casting, spin or spray deposition, or by means of mechanical pressing. In one embodiment, the thin film is produced by solution casting where the blend of polymers are dissolved in a solvent and then cast on a solid surface. The solvent utilized depends on the polymers used in the blend and on their particular dissolution characteristics. Solvents for solvent casting may be chosen from aqueous solutions in addition to the solvents described in section (III)(a)(ii). In one preferred embodiment, the solvent is dioxane.

The ratio of the additional polymer to the polymer or copolymer having the repeat unit of Formula (I) can and will vary. In some embodiments, the weight ratio of the polymer or copolymer comprising the repeat unit of Formula (I) to the additional polymer may be about 99:1, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, 5:95, or 1:99 weight %. In preferred embodiments, the ratio of the polymer or copolymer comprising the repeat unit of Formula (I) to the additional polymer is 15:85, 90:10, or 95:5.

In preferred embodiments, a homopolymer or copolymer comprising a repeat unit of Formula (III) is blended with poly(lactic) acid to form a thin film. In one embodiment, the ratio of the polymer or copolymer comprising Formula (III) to the poly(lactic) acid is 15:85. In another embodiment, the ratio of the polymer or copolymer comprising Formula (III) to the poly(lactic) acid is 10:90. In still another embodiment, the ratio of the polymer or copolymer comprising Formula (III) to the poly(lactic) acid is 5:95.

In various aspects, the thin film may have characteristics of brittleness, crystallinity (as measured by differential scanning calorimetry (DSC) and wide angle X-ray diffractometry (WXRD)), elongation, hardness, flexural strength, stiffness (as measured by Young's modulus), shrinkage, surface morphology (as determined by scanning electron microscopy (SEM)), stretch, and tensile strength as well as visual characteristics such as transparency or opacity.

(V) Feed Compositions

In another aspect, the compounds described herein may be used as feed composition or feed pre-mix. In some aspects, the feed compositions are designed to provide a nutritive agent to a subject. The feed composition/pre-mix may be formulated as liquids, emulsions, dry pellets, or powders and may be mixed with various other ingredients.

The feed composition comprises a homopolymer or copolymer as described in sections (I) or (II). The hydrolysis product of the homopolymer or copolymer as described in section (I) or (II) may be a nutritive agent. In other words, when the monomeric form of the homopolymer or copolymer is released by hydrolysis, the resulting free monomer may act as a nutritive. In one embodiment, the nutritive agent may be a methionine source. In another embodiment, the nutritive agent may be a gluconeogenetic precursor, for example valeric acid.

Generally, the feed composition is administered to a subject orally. The subject may be an animal or a human subject. Non-limiting examples of suitable animal subjects include companion animals such as cats, dogs, rabbits, horses, and rodents such as gerbils; agricultural animals such as cows, dairy cows, dairy calves, beef cattle, pigs, goats, sheep, horses, deer; zoo animals such as primates, elephants, zebras, large cats, bears, and the like; and research animals such as rabbits, sheep, pigs, dogs, primates, mice, rats and other rodents. In other aspects, the compositions may be provided to an avian subject, including but not limited to chickens, ducks, turkeys, ostrich, and emu. In still another aspect, the subject may be an aquaculture subject chosen from fish and crustaceans including, but not limited to, salmon, shrimp, carp, tilapia, and shell fish.

The subject may be monogastric or a ruminant. Where the animal is a ruminant, the homopolymers and copolymers described in section (I) or (II) remain substantially intact in the rumen and hydrolyze after passage through the rumen. The stability in the rumen may lead to increased feed efficiency for the homopolymer or copolymer in ruminant animals.

A substantially intact composition may be characterized by a low level of free monomer where less than 25% of the homopolymer or copolymer is hydrolyzed to a free monomer. In some aspects, a substantially intact homopolymer or copolymer may be less than about 10% monomer, or less than 9%, 8%, 7%, 6%, 5%, 4%, 3%, 2%, or more preferably, less than about 1% monomer.

The homopolymers and copolymers described herein may hydrolyze after passage from the rumen. For example, the homopolymers and copolymers may hydrolyze under conditions where the homopolymers and copolymers are subjected to a pH of about 5, 4.5, 4, 3.5, 3, 2.5, 2, 1.5, 1, or 0.5, or any pH between and including the listed values. A substantially hydrolyzed composition, as used herein, refers to a solution where greater than 30% of the composition described in section (I) or (II) is free monomer. In some aspects, a substantially hydrolyzed composition may have a free monomer content of about 50%, or 60% or greater. In some aspects, a substantially hydrolyzed composition may have a free monomer content of about 80% or greater.

In some embodiments, the feed may be provided as feed compositions or feed premixes which may be combined with various other ingredients. In some embodiments, the feed composition/premix comprises one or more homopolymers or copolymers as described in section (I) or (II) and additional ingredients which may be chosen from one or more of the following: carbohydrates, fats, proteins, amino acids, and alpha hydroxy acids.

Suitable protein sources may be animal-derived proteins, plant-derived proteins, or combinations thereof. In some embodiments, suitable sources of animal derived protein include blood meal, bone meal, fish meal, fish processing by-products, meat meal, meat and bone meal, poultry byproduce meal, feather meal, and combinations thereof. In other embodiments, suitable sources of plant-derived proteins include grains such as corn, oats, soybean, and the like; grain protein concentrates such as soy protein concentrate; legumes such as peas, lupine, alfalfa; distiller's grains; oilseed meals such as canola meal, cottonseed meal, flaxseed meal, soybean meal, sunflower seed meal; and combinations thereof.

In yet another embodiment, the feed composition/premix includes a fat source. The fat source may be an inert fat or a non-inert fat. Non-limiting examples of non-inert fats include plant derived oils (e.g., canola oil, corn oil, cottonseed oil, palm oil, peanut oil, safflower oil, soybean oil, and sunflower oil), fish oils (e.g., menhaden oil, anchovy oil, albacore tuna oil, cod liver oil, herring oil, lake trout oil, mackerel oil, salmon oil, and sardine oil), animal fats (e.g., poultry fat, beef tallow, butter, pork lard, and whale blubber), yellow grease (i.e., waste grease from restaurants and low-grade fats from rendering plants), and combinations thereof. The non-inert fat source may also be a high fat product such as fish meal (e.g., menhaden meal, anchovy meal, herring meal, pollack meal, salmon meal, tuna meal, and whitefish meal), oilseeds (e.g., canola seeds, cottonseeds, flax seeds, linseeds, *Niger* seeds, sesame seeds, soy beans, and sunflower seeds), or distillers grains (e.g., dried distillers grains and solubles (DDGS) and wet distillers grains). The fat source may be a ruminally inert fat. Suitable examples of ruminally inert fats include calcium salts of palm fatty acids (e.g., MEGALAC®), saturated free fatty acids, or hydrogenated tallow (e.g., ALIFET®).

The feed composition/premix may additionally comprise a carbohydrate source. Suitable carbohydrates may be chosen from those known in the art and include, without limitation, alginate, arrowroot, barley, canola, cassava, corn, corn syrup, cottonseed meal, fructose, glucose, galactose, grain sorghum, kelp meal, lactose, maize, maltose, mannose, potatoes, oats, rice, rye, sago, sorbitol, soybeans, tapioca, wheat, wheat gluten, yam, and combinations thereof.

In some embodiments, the feed composition/premix may include one or more alpha acids including amino acids and alpha hydroxy acids. Suitable examples of amino acids, depending upon the formulation, include alanine, arginine, asparagines, aspartate, cysteine, glutamate, glutamine, glycine, histidine, isoleucine, leucine, lysine, methionine, selenomethionine, phenylalanine, proline, serine, threonine, tryptophan, tyrosine, and valine. Other amino acids usable as feed additives include, by way of non-limiting example, N-acylamino acids, hydroxy homologue compounds, and physiologically acceptable salts thereof, such as hydrochlorides, hydrosulfates, ammonium salts, potassium salts, calcium salts, magnesium salts and sodium salts of amino acids. The feed compositions may further include an alpha hydroxy acid. In some aspects the alpha hydroxy acids are alpha hydroxy analogs of amino acids. In one aspect, the alpha acid is the hydroxy analog of methionine.

(VI) Combinations with Nutritive and Pharmaceutical Agents

The homopolymers and copolymers of the invention may be combined with a nutritive agent and/or a pharmaceutically acceptable agent. Nutritive agents may comprise any agent that provides nutritive value when administered to the subject. Non-limiting examples of nutritive agents include vitamin, mineral (e.g., organic or inorganic), antioxidant, organic acid, poly unsaturated fatty acid ("PUFA"), prebiotic, probiotic, herb, and pigments.

Suitable vitamins include vitamin C, vitamin A, vitamin E, vitamin B12, vitamin K, riboflavin, niacin, vitamin D, vitamin B6, folic acid, pyridoxine, thiamine, pantothenic acid, and biotin. The form of the vitamin may include salts of the vitamin, derivatives of the vitamin, compounds having the same or similar activity of a vitamin, and metabolites of a vitamin.

Suitable organic trace mineral may comprise a metal chelate comprising metal ions and an amino acid ligand. Alternatively, the organic trace mineral may be a metal salt comprising metal ions and an amino acid anion. The metal ions may be selected from the group consisting of zinc ions, copper ions, manganese ions, iron ions, chromium ions, cobalt ions, magnesium ions, calcium ions, and combinations thereof. In a preferred embodiment, the metal ions are zinc ions, manganese ions, and copper ions. The amino acids may be selected from the group comprising alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, or their hydroxy analogs. In certain embodiments, the copper and zinc ions are preferably divalent, i.e., each ion carries a charge of $2^+$. The molar ratio of amino acids to metal ions in the chelate molecule may generally vary from 1:1 to 3:1 or higher. Typically, a metal chelate may comprise a mixture of 1:1, 2:1 and 3:1 species. Preferably, the molar ratio of amino acids to metal ion in the chelate molecule may generally vary from 1.5:1 to 2.5:1. In an aqueous medium, the relative proportions of these species are determined by the applicable stability constants. Where the number of ligands equates to the charge on the metal ion, the charge is typically balanced because the carboxyl moieties of the amino acids are in deprotonated form. For example, in the chelate species wherein the metal cation carries a charge of 2+ and the amino acid to metal ratio is 2:1, each of the hydroxy or amino groups is understood to be bound by a coordinate covalent bond to the metal ion. Where the number of ligands exceeds the charge on the metal ion, e.g., in a 3:1 chelate of a divalent metal ion, the amino acids in excess of the charge typically may remain in a protonated state to balance the charge. On the other hand, where the positive charge on the metal ion exceeds the number of amino acids, the charge may be balanced by the presence of another anion such as, for example, chloride, bromide, iodide, bicarbonate, hydrogen sulfate, dihydrogen phosphate and combinations thereof. Divalent anions may also be present. In an exemplary embodiment, the metal chelate comprises 2-hydroxy-4-methylthiobutanoic acid.

The mineral may also be an inorganic trace mineral. Suitable inorganic trace minerals include, for example, metal sulfates, metal oxides, metal carbonates, and metal halides. By way of non-limiting example, the inorganic trace mineral may be copper sulfate, copper oxide, copper chloride, or copper carbonate. Alternatively, the inorganic trace mineral may be manganese sulfate, manganese chloride, or manganous oxide. In another embodiment, the inorganic trace mineral may be zinc sulfate, zinc oxide, zinc chloride, or zinc carbonate. In yet an additional embodiment, the inorganic trace mineral may be sodium selenite or sodium selenate.

Suitable antioxidants include, but are not limited to, ascorbic acid and its salts, ascorbyl palmitate, ascorbyl stearate, anoxomer, n-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline (ethoxyquin), ethyl gallate, ethyl maltol, ethylenediaminetetraacetic acid (EDTA), *eucalyptus* extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, n-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof.

A variety of organic acids comprised of carboxylic acids are suitable. In one embodiment, the organic acid may contain from about one to about twenty-five carbon atoms. In another embodiment, the organic acid may have from about three to about twenty-two carbon atoms. In a further embodiment, the organic acid may contain from about three to about twelve carbon atoms. In yet another embodiment, the organic acid may contain from about eight to about twelve carbon atoms. In still another embodiment, the organic acid may contain from about two to about six carbon atoms. Suitable organic acids, by way of non-limiting example, include formic acid, acetic acid, propionic acid, butanoic acid, benzoic acid, lactic acid, malic acid, tartaric acid, mandelic acid, citric acid, fumaric acid, sorbic acid, boric acid, succinic acid, adipic acid, glycolic acid, cinnamaldehyde, and glutaric acid.

Salts of organic acids comprising carboxylic acids are also suitable for certain embodiments. Representative suitable salts include the ammonium, magnesium, calcium, lithium, sodium, potassium, selenium, iron, copper, and zinc salts of organic acids. In one embodiment, the organic acid is an ammonium, magnesium, calcium, lithium, sodium, potassium, selenium, iron, copper, or zinc salt of formic acid. In another embodiment, the organic acid is an ammonium, magnesium, calcium, lithium, sodium, potassium, selenium, iron, copper, or zinc salt of acetic acid. In yet another embodiment, the organic acid is an ammonium, magnesium, calcium, lithium, sodium, potassium, selenium, iron, copper, or zinc salt of propionic acid. In an additional embodiment, the organic acid is an ammonium, magnesium, calcium, lithium, sodium, potassium, selenium, iron, copper, or zinc salt of butanoic acid. In a further embodiment, the organic acid is an ammonium, magnesium, calcium, lithium, sodium, potassium, selenium, iron, copper, or zinc salt of benzoic acid. In still another embodiment, the organic acid is an ammonium, magnesium, calcium, lithium, sodium, potassium, selenium, iron, copper, or zinc salt of lactic acid. In yet another embodiment, the organic acid is an ammonium, magnesium, calcium, lithium, sodium, potassium, selenium, iron, copper, or zinc salt of malic acid. In still another embodiment, the organic acid is an ammonium, magnesium, calcium, lithium, sodium, potassium, selenium, iron, copper, or zinc salt of tartaric acid. In a further embodiment, the organic acid is an ammonium, magnesium, calcium, lithium, sodium, potassium, selenium, iron, copper, or zinc salt of mandelic acid. In yet another embodiment, the organic acid is an ammonium, magnesium, calcium, lithium, sodium, potassium, selenium, iron, copper, or zinc salt of citric acid. In an additional embodiment, the organic acid is an ammonium, magnesium, calcium, lithium, sodium, potassium, selenium, iron, copper, or zinc salt of fumaric acid. In an additional embodiment, the organic acid is an ammonium, magnesium, calcium, lithium, sodium, potassium, selenium, iron, copper, or zinc salt of sorbic acid. In another embodiment, the organic acid is an ammonium, magnesium, calcium, lithium, sodium, potassium, selenium, iron, copper, or zinc salt of boric acid. In yet another embodiment, the organic acid is an ammonium, magnesium, calcium, lithium, sodium, potassium, selenium, iron, copper, or zinc salt of succinic acid. In another embodiment, the organic acid is an ammonium, magnesium, calcium, lithium, sodium, potassium, selenium, iron, copper, or zinc salt of adipic acid. In yet another embodiment, the organic acid is an ammonium, magnesium, calcium, lithium, sodium, potassium, selenium, iron, copper, or zinc salt of glycolic acid. In an additional embodiment, the organic acid is an ammonium, magnesium, calcium, lithium, sodium, potassium, selenium, iron, copper, or zinc salt of glutaric acid.

Alternatively, the organic acid may be comprised of a substituted carboxylic acid. A substituted carboxylic acid generally has the same features as those detailed above for carboxylic acids, but the hydrocarbyl chain has been modified such that it is branched, is part of a ring structure, or contains some other substitution. In one embodiment, the substituted carboxylic acid may contain one or more additional carboxyl groups. Saturated dicarboxylic acids include malonic acid, succinic acid, glutaric acid, and adipic acid, and unsaturated dicarboxylic acids include maleic acid and fumaric acid. In another embodiment, the substituted carboxylic acid may contain one or more hydroxy groups. A substituted carboxylic acid with a hydroxy group on the alpha carbon, i.e., the carbon adjacent to the carboxyl carbon, is generally called a α-hydroxy carboxylic acid. Examples of suitable α-hydroxy carboxylic acids include glycolic acid, lactic acid, malic acid, and tartaric acid. In an alternate embodiment, the substituted carboxylic acid may contain one or more carbonyl groups. In yet another embodiment, the substituted carboxylic acid may contain an amino group on the alpha carbon, i.e., is an α-amino acid. In one embodiment, the α-amino acid may be one of the twenty standard amino acids or derivatives thereof. In another embodiment, the α-amino acid may be an essential α-amino acid selected from the group consisting of arginine, histidine, isoleucine, leucine, lysine, methionine, phenylalanine, threonine, tryptophan, and valine. Salts of organic acids comprising substituted carboxylic acids are also suitable for certain embodiments. Representative suitable salts include the ammonium, magnesium, calcium, lithium, sodium, potassium, selenium, iron, copper, and zinc salts of organic acids comprising substituted carboxylic acids.

Suitable PUFAs include a long chain fatty acid with at least 18 carbon atoms and at least two carbon-carbon double bonds, generally in the cis-configuration. In an exemplary embodiment, the PUFA is an omega fatty acid. The PUFA may be an omega-3 fatty acid in which the first double bond occurs in the third carbon-carbon bond from the methyl end of the carbon chain (i.e., opposite the carboxyl acid group). Suitable examples of omega-3 fatty acids include all-cis 7,10, 13-hexadecatrienoic acid; all-cis-9,12,15-octadecatrienoic acid (alpha-linolenic acid, ALA); all-cis-6,9,12,15,-octadecatetraenoic acid (stearidonic acid); all-cis-8,11,14,17-eicosatetraenoic acid (eicosatetraenoic acid); all-cis-5,8,11,14, 17-eicosapentaenoic acid (eicosapentaenoic acid, EPA); all-cis-7,10,13,16,19-docosapentaenoic acid (clupanodonic acid, DPA); all-cis-4,7,10,13,16,19-docosahexaenoic acid (docosahexaenoic acid, DHA); all-cis-4,7,10,13,16,19-docosahexaenoic acid; and all-cis-6,9,12,15,18,21-tetracosenoic acid (nisinic acid). In an alternative embodiment, the PUFA may be an omega-6 fatty acid in which the first double bond occurs in the sixth carbon-carbon bond from the methyl end of the carbon chain. Examples of omega-6 fatty acids include all-cis-9,12-octadecadienoic acid (linoleic acid); all-cis-6,9,12-octadecatrienoic acid (gamma-linolenic acid, GLA); all-cis-11,14-eicosadienoic acid (eicosadienoic acid); all-cis-8,11,14-eicosatrienoic acid (dihomo-gamma-linolenic acid, DGLA); all-cis-5,8,11,14-eicosatetraenoic acid (arachidonic acid, AA); all-cis-13,16-docosadienoic acid (docosadienoic acid); all-cis-7,10,13,16-docosatetraenoic acid (adrenic acid); and all-cis-4,7,10,13,16-docosapentaenoic acid (docosapentaenoic acid). In yet another alternative embodiment, the PUFA may be an omega-9 fatty acid in which the first double bond occurs in the ninth carbon-carbon bond from the methyl end of the carbon chain, or a conjugated fatty acid, in which at least one pair of double bonds are separated by only one single bond. Suitable examples of omega-9 fatty acids include cis-9-octadecenoic acid (oleic acid); cis-11-eicosenoic acid (eicosenoic acid); all-cis-5,8, 11-eicosatrienoic acid (mead acid); cis-13-docosenoic acid (erucic acid), and cis-15-tetracosenoic acid (nervonic acid). Examples of conjugated fatty acids include 9Z,11E-octadeca-9,11-dienoic acid (rumenic acid); 10E,12Z-octadeca-9, 11-dienoic acid; 8E,10E,12Z-octadecatrienoic acid (α-calendic acid); 8E,10E,12E-octadecatrienoic acid (β-Calendic acid); 8E,10Z,12E-octadecatrienoic acid (jacaric acid); 9E,11E,13Z-octadeca-9,11,13-trienoic acid (a-eleostearic acid); 9E,11E,13E-octadeca-9,11,13-trienoic acid (1-eleostearic acid); 9Z,11Z,13E-octadeca-9,11,13-trienoic acid (catalpic acid), and 9E,11Z,13E-octadeca-9,11,13-trienoic acid (punicic acid).

Probiotics and prebiotics may include yeast and bacteria that help establish an immune protective rumen or gut microflora as well as small oligosaccharides. By way of non-limiting example, yeast-derived probiotics and prebiotics include yeast cell wall derived components such as β-glucans, arabinoxylan isomaltose, agarooligosaccharides, lactosucrose, cyclodextrins, lactose, fructooligosaccharides, laminariheptaose, lactulose, β-galactooligosaccharides, mannanoligosaccharides, raffinose, stachyose, oligofructose, glucosyl sucrose, sucrose thermal oligosaccharide, isomalturose, caramel, inulin, and xylooligosaccharides. In an exemplary embodiment, the yeast-derived agent may be β-glucans and/or mannanoligosaccharides. Sources for yeast cell wall derived components include *Saccharomyces bisporus, Saccharomyces boulardii, Saccharomyces cerevisiae, Saccharomyces capsularis, Saccharomyces delbrueckii, Saccharomyces fermentati, Saccharomyces lugwigii, Saccharomyces microellipsoides, Saccharomyces pastorianus, Saccharomyces rosei, Candida albicans, Candida cloaceae, Candida tropicalis, Candida utilis, Geotrichum candidum, Hansenula americana, Hansenula anomala, Hansenula wingei,* and *Aspergillus oryzae.*

Probiotics and prebiotics may also include bacteria cell wall derived agents such as peptidoglycan and other components derived from gram-positive bacteria with a high content of peptidoglycan. Exemplary gram-positive bacteria include *Lactobacillus acidophilus, Bifedobact thermophilum, Bifedobat longhum, Streptococcus faecium, Bacillus pumilus, Bacillus subtilis, Bacillus licheniformis, Lactobacillus acidophilus, Lactobacillus casei, Enterococcus faecium, Bifidobacterium bifidium, Propionibacterium acidipropionici, Propionibacteriium freudenreichii,* and *Bifidobacterium pscudolongum.*

Suitable herbals and herbal derivatives, as used herein, refer to herbal extracts, and substances derived from plants and plant parts, such as leaves, flowers and roots, without limitation. Non-limiting exemplary herbals and herbal derivatives include agrimony, alfalfa, aloe vera, amaranth, *angelica,* anise, barberry, basil, bayberry, bee pollen, birch, bistort, blackberry, black cohosh, black walnut, blessed thistle, blue cohosh, blue vervain, boneset, borage, buchu, buckthorn, bugleweed, burdock, *capsicum,* cayenne, caraway, cascara sagrada, catnip, celery, centaury, chamomile, chaparral, chickweed, chicory, chinchona, cloves, coltsfoot, comfrey, cornsilk, couch grass, cramp bark, culver's root, cyani, cornflower, damiana, dandelion, devils claw, dong quai, *echinacea,* elecampane, ephedra, *eucalyptus,* evening primrose, eyebright, false unicorn, fennel, fenugreek, figwort, flaxseed, garlic, gentian, ginger, *ginseng,* golden seal, gotu kola, gum weed, hawthorn, hops, horehound, horseradish, horsetail, hoshouwu, *hydrangea,* hyssop, iceland moss, irish moss, jojoba, juniper, kelp, lady's slipper, lemon grass, licorice, *lobelia,* mandrake, marigold, marjoram, marshmallow, mistletoe, mullein, mustard, myrrh, nettle, oatstraw, oregon grape, *papaya,* parsley, passion flower, peach, pennyroyal, peppermint, periwinkle, plantain, pleurisy root, pokeweed, prickly ash, *psyllium,* quassia, queen of the meadow, red clover, red raspberry, redmond clay, rhubarb, rose hips, rosemary, rue, safflower, saffron, sage, St. John's wort, sarsaparilla, *sassafras,* saw palmetto, scullcap, senega, *senna,* shepherd's purse, slippery elm, spearmint, spikenard, squawvine, stillingia, strawberry, taheebo, thyme, uva *ursi,* valerian, violet, watercress, white oak bark, white pine bark, wild cherry, wild lettuce, wild yam, willow, wintergreen, witch hazel, wood betony, wormwood, yarrow, yellow dock, yerba santa, *yucca* and combinations thereof.

Suitable non-limiting pigments include actinioerythrin, alizarin, alloxanthin, β-apo-2'-carotenal, apo-2-lycopenal, apo-6'-lycopenal, astacein, astaxanthin, azafrinaldehyde, aacteriruberin, aixin, α-carotine, β-carotine, γ-carotine, β-carotenone, canthaxanthin, capsanthin, capsorubin, citranaxanthin, citroxanthin, crocetin, crocetinsemialdehyde, crocin, crustaxanthin, cryptocapsin, α-cryptoxanthin, β-cryptoxanthin, cryptomonaxanthin, cynthiaxanthin, decaprenoxanthin, dehydroadonirubin, diadinoxanthin, 1,4-diamino-2,3-dihydroanthraquinone, 1,4-dihydroxyanthraquinone, 2,2'-Diketospirilloxanthin, eschscholtzxanthin, eschscholtzxanthone, flexixanthin, foliachrome, fucoxanthin, gazaniaxanthin, hexahydrolycopene, hopkinsiaxanthin, hydroxyspheriodenone, isofucoxanthin, loroxanthin, lutein, luteoxanthin, lycopene, lycopersene, lycoxanthin, morindone, mutatoxanthin, neochrome, neoxanthin, nonaprenoxanthin, OH-Chlorobactene, okenone, oscillaxanthin, paracentrone, pectenolone, pectenoxanthin, peridinin, phleixanthophyll, phoeniconone, phoenicopterone, phoenicoxanthin, physalien, phytofluene, pyrrhoxanthininol, quinones, rhodopin, rhodopinal, rhodopinol, rhodovibrin, rhodoxanthin, rubixanthone, saproxanthin, semi-α-carotenone, semi-β-carotenone, sintaxanthin, siphonaxanthin, siphonein, spheroidene, tangeraxanthin, torularhodin, torularhodin methyl ester, torularhodinaldehyde, torulene, 1,2,4-trihydroxyanthraquinone, triphasiaxanthin, trollichrome, vaucheriaxanthin, violaxanthin, wamingone, xanthin, zeaxanthin, α-zeacarotene and combinations thereof.

Suitable non-limiting pharmaceutically acceptable agents include an acid/alkaline-labile drug, a pH dependent drug, or a drug that is a weak acid or a weak base. Examples of acid-labile drugs include statins (e.g., pravastatin, fluvastatin and atorvastatin), antiobiotics (e.g., penicillin G, ampicillin, streptomycin, erythromycin, clarithromycin and azithromycin), nucleoside analogs [e.g., dideoxyinosine (ddI or didanosine), dideoxyadenosine (ddA), dideoxycytosine (ddC)], salicylates (e.g., aspirin), digoxin, bupropion, pancreatin, midazolam, and methadone. Drugs that are only soluble at acid pH include nifedipine, emonapride, nicardipine, amosulalol, noscapine, propafenone, quinine, dipyridamole, josamycin, dilevalol, labetalol, enisoprost, and metronidazole. Drugs that are weak acids include phenobarbital, phenytoin, zidovudine (AZT), salicylates (e.g., aspirin), propionic acid compounds (e.g., ibuprofen), indole derivatives (e.g., indomethacin), fenamate compounds (e.g., meclofenamic acid), pyrrolealkanoic acid compounds (e.g., tolmetin), cephalosporins (e.g., cephalothin, cephalaxin, cefazolin, cephradine, cephapirin, cefamandole, and cefoxitin), 6-fluoroquinolones, and prostaglandins. Drugs that are weak bases include adrenergic agents (e.g., ephedrine, desoxyephedrine, phenylephrine, epinephrine, salbutamol, and terbutaline), cholinergic agents (e.g., physostigmine and neostigmine), antispasmodic agents (e.g., atropine, methantheline, and papaverine), curariform agents (e.g., chlorisondamine), tranquilizers and muscle relaxants (e.g., fluphenazine, thioridazine, trifluoperazine, chlorpromazine, and triflupromazine), antidepressants (e.g., amitriptyline and nortriptyline), antihistamines (e.g., diphenhydramine, chlorpheniramine, dimenhydrinate, tripelennamine, perphenazine, chlorprophenazine, and chlorprophenpyridamine), cardioactive agents (e.g., verapamil, diltiazem, gallopomil, cinnarizine, propranolol, metoprolol and nadolol), antimalarials (e.g., chloroquine), analgesics (e.g., propoxyphene and meperidine), antifungal agents (e.g., ketoconazole and itraconazole), antimicrobial agents (e.g., cefpodoxime, proxetil, and enoxacin), caffeine, theophylline, and morphine. In another embodiment, the drug may be a biphosphonate or another drug used to treat osteoporosis. Non-limiting examples of a biphosphonate include alendronate, ibandronate, risedronate, zoledronate, pamidronate, neridronate, olpadronate, etidronate, clodronate, and tiludronate. Other suitable drugs include estrogen, selective estrogen receptor modulators (SERMs), and parathyroid hormone (PTH) drugs. In yet another embodiment, the drug may be an antibacterial agent. Suitable antibiotics include aminoglycosides (e.g., amikacin, gentamicin, kanamycin, neomycin, netilmicin, streptomycin, and tobramycin), carbecephems (e.g., loracarbef) a carbapenem (e.g., certapenem, imipenem, and meropenem), cephalosporins (e.g., cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone), macrolides (e.g., azithromycin, clarithromycin, dirithromycin, erythromycin, and troleandomycin), monobactam, penicillins (e.g., amoxicillin, ampicillin, carbenicillin, cloxacillin, dicloxacillin, nafcillin, oxacillin, penicillin G, penicillin V, piperacillin, and ticarcillin), polypeptides (e.g., bacitracin, colistin, and polymyxin B), quinolones (e.g., ciprofloxacin, enoxacin, gatifloxacin, levofloxacin, lomefloxacin, moxifloxacin, norfloxacin, ofloxacin, and trovafloxacin), sulfonamides (e.g., mafenide, sulfacetamide, sulfamethizole, sulfasalazine, sulfisoxazole, and trimethoprim-sulfamethoxazole), and tetracyclines (e.g., demeclocycline, doxycycline, minocycline, and oxytetracycline). In an alternate embodiment, the drug may be an antiviral protease inhibitor (e.g., amprenavir, fosamprenavir, indinavir, lopinavir/ritonavir, ritonavir, saquinavir, and nelfinavir). In a still another embodiment, the drug may be a cardiovascular drug. Examples of suitable cardiovascular agents include cardiotonic agents (e.g., *digitalis* (digoxin), ubidecarenone, and dopamine), vasodilating agents (e.g., nitroglycerin, captopril, dihydralazine, diltiazem, and isosorbide dinitrate), antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril), beta blockers (e.g., levobunolol, pindolol, timolol maleate, bisoprolol, carvedilol, and butoxamine), alpha blockers (e.g., doxazosin, prazosin, phenoxybenzamine, phentolamine, tamsulosin, alfuzosin, and terazosin), calcium channel blockers (e.g., amlodipine, felodipine, nicardipine, nifedipine, nimodipine, nisoldipine, nitrendipine, lacidipine, lercanidipine, verapamil, gallopamil, and diltiazem), and anticlot agents (e.g., dipyrimadole).

A variety of commonly used excipients in pharmaceutical and nutritive formulations may be utilized with any such agents described above. Non-limiting examples of suitable excipients include an agent selected from the group consisting of non-effervescent disintegrants, a coloring agent, a flavor-modifying agent, an oral dispersing agent, a stabilizer, a preservative, a diluent, a compaction agent, a lubricant, a filler, a binder, taste masking agents, an effervescent disintegration agent, and combinations of any of these agents.

The compositions described in section (I) or (II) may be configured with the pharmaceutical or nutritive including as a coating or matrix encapsulating the pharmaceutical or nutritive.

DEFINITIONS

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2=CH—CH_2—$), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The term "crystalline polymer" as used herein refers to a polymer having the characteristic or regular three-dimensional packing.

The term "enrichment" means an amount above the statistical distribution if all chiral centers had an equal probability of being alpha or beta.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "epoxy" or "epoxide" as used herein means a cyclic ether. The ring structure generally comprises from 2 to 5 carbon atoms in the ring.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting a particular moiety, wherein the protecting group may be removed, subsequent to the reaction for which the protection is employed, without disturbing the remainder of the molecule. A variety of protecting groups and the synthesis thereof may be found in "Protective Groups in Organic Synthesis" by T.W. Greene and P.G.M. Wuts, John Wiley & Sons, 1999.

The term "semi-crystalline polymer" as used herein refers to a polymer with regions that are "crystalline" as describe above, and regions that are amorphous, having no regular packing to the three-dimensional structure.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

Having described the invention in detail, it will be apparent that modifications and variations are possible without departing from the scope of the invention defined in the appended claims.

EXAMPLES

Example 1

Preparation of Polymer 1

2-hydroxy-4-(methylthio)-butanoic acid (HMTBA) (150.0 g, 92%) was mixed with xylenes (120.0 g) and water was azeotropically distilled at 120.0° C.-135.0° C. for 3-4 h under nitrogen. Once the theoretical amount of water was removed, the flask was connected to a standard vacuum distillation apparatus where the pressure was reduced to ca. 195 mmHg and the temperature of the heating bath was kept constant at 120.0° C. for several (4-6 h) hours. During this phase, condensation water was collected indicating that polymerization is taking place. Then, the bath temperature was raised to 165° C. and the reaction was heated for another 4 h. The Polymer was analyzed by Liquid Chromatography Mass Spectrometry (LC/MS).

Example 2

Preparation of Polymer 2

HMTBA (50-225 g, 1.34% water) and xylenes (20-1000 mL) were charged in a 100-500 mL round bottom flask and azeotropically distilled under nitrogen at 120-150° C. for 4-5 h to collect theoretical amount of water. Stannous Octoate catalyst (0.15-0.2 wt %) was added to heterogeneous dispersion of HMTBA/Xylenes and initiated polymerization at 140-150° C. and at pressure 195 mmHg. Temperature was increased to 170.0° C. in 3-4 h (10° C./h), and reduced pressure to 30 mmHg in 5-6 h. Polymerization was continued at 30 mmHg and at 170.0° C. for another 3-5 hours. Highly viscous brownish yellow polymers were obtained.

The resulting polymer was collected and analyzed for relative composition by LC/MS and High Performance Liquid Chromatorgraphy (HPLC) and molecular weight (GPC). The polymer (1 mg) was dissolved in acetonitrile and filtered prior to HPLC or LC/MS injection.

Example 3

Gel Permeation Chromatography Analysis

Polymer samples were dissolved in chloroform with a target concentration of 2 mg/mL. An aliquot of the sample was transferred to an autosampler vial and analyzed using GPC with evaporative light scattering detector (ELSD).

Two different sets of polystyrene standards were chosen to construct calibration curves for polymer characterization. Polystyrene calibration standard solutions with peak average molecular weights (Mp) in the range of 370 to 4430 g/mol and weight average molecular weight (Mw) of 423 to 4679 g/mol were prepared in chloroform at concentrations of ~1 mg/mL for polymer 1 whereas polystyrene calibration standard solutions with peak average molecular weights (Mp) in the range of 370 to 10210 g/mol and weight average molecular weight (Mw) of 423 to 10290 g/mol were prepared in chloroform at concentrations of ~1 mg/mL for polymer 2 characterization.

Calibration curves were constructed with log(Mp) versus retention time for the polystyrene calibration standard solutions using a linear model equation and r2 value of 0.999.

Figure 2:
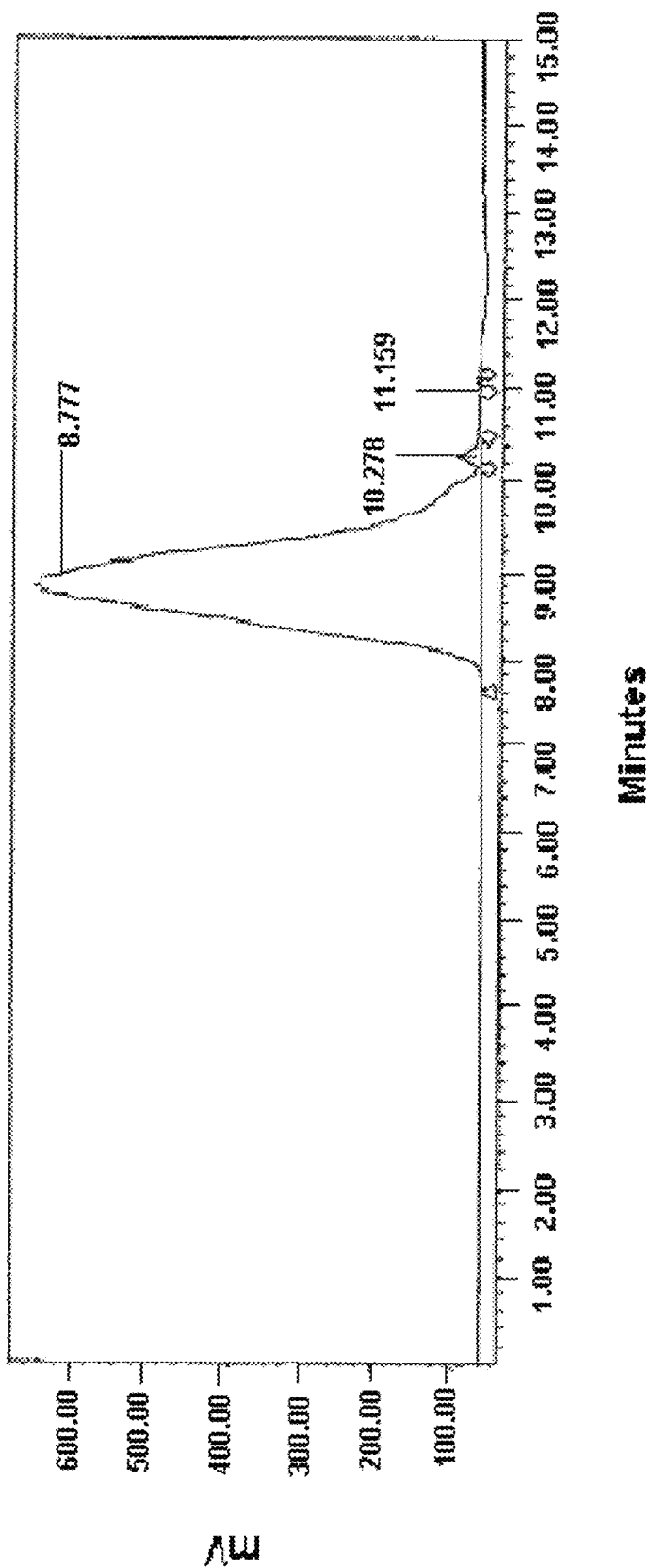
FIG. 2 is a gel permeation chromatogram of polymer 2, a homopolymer of 2-hydroxy-4-(methylthio)-butanoic acid (HMTBA).
Figure 3A:
FIG. 3A shows a thin film made from a 85:15 ratio of 20 KDa poly(lactic) acid and an HMTBA homopolymer.
Figure 3B:
FIG. 3B shows a thin film made from a 90:10 ratio of 20 KDa poly(lactic) acid and an HMTBA homopolymer.
Figure 3C:
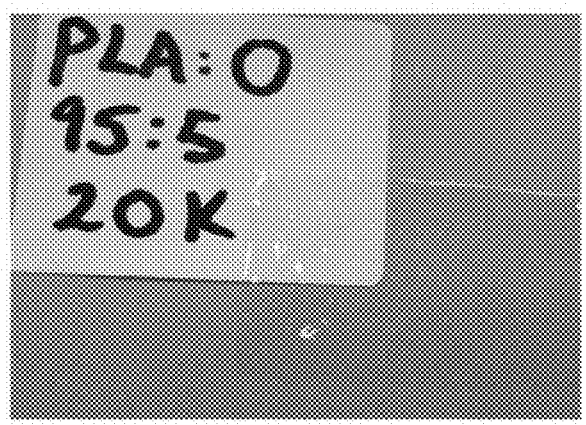
FIG. 3C shows a thin film made from a 95:5 ratio of 20 KDa poly(lactic) acid and an HMTBA homopolymer.
Figure 3D:
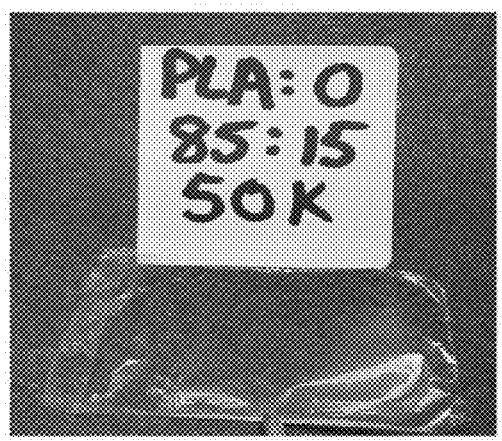
FIG. 3D shows a thin film made from a 85:15 ratio of 50 KDa poly(lactic) acid and an HMTBA homopolymer.
Figure 3E:
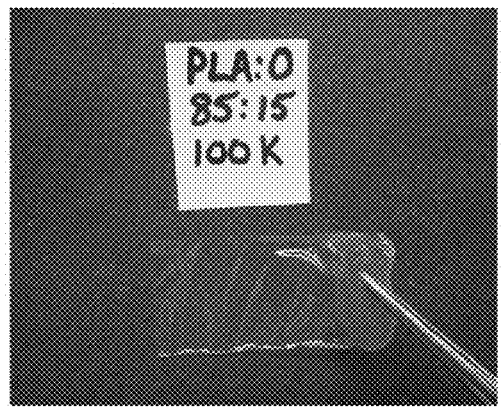
FIG. 3E shows a thin film made from a 85:15 ratio of 100 KDa poly(lactic) acid and an HMTBA homopolymer.

For sample processing, test material GPC chromatograms were sliced into 0.2 minute increments, and each slice retention time was converted to the corresponding MW using the calibration curve. The mobile phase was chloroform. Table 1 and FIGS. 1 and 2 show the GPC characterization results for all polymers.

TABLE 1

GPC Studies

| Sample Id | Retention Time (min) | Mn | Mw | PDI |
|---|---|---|---|---|
| Polymer 1 | 7.52 | 310 | 481 | 1.55 |
| Polymer 2 | 8.77 | 1423 | 2293 | 1.61 |

*Number average Molecular Weight Mn = $\Sigma n_i / \Sigma n_i/M_i$), Mw: Weight Average Molecular Weight (Mw = $\Sigma n_i M_i / \Sigma n_i$), PDI = Polydispersity Index (Mw/Mn).

Example 4

Polymer Films

Films were casted using commercially available poly(lactic) acid having molecular weights of 20, 30, 50, and 100 KDa and the compositions of the invention comprising HMTBa homopolymer (Polymer) having a molecular weight of 0.5-0.6 KDa. A 1-2 g of PLA/Polymer of various ratios was dissolved in 10-20 mL of dioxane to yield syrupy/honey like liquids. Films were casted on microscopic slide by spreading the syrupy liquid with glass rod or dropping liquid to cover entire surface using a pipette. Excess liquid was drawn out of slide by rolling glass rod. Films were placed on hot plate at 60-70° C. to evaporate solvent and dried at ambient temperature for 15-20 min. Then films were peeled off slide using razor blade. Off all combinations of PLA/Polymer tested 85/15, 90/10, and 95/5 formed clear, flexible, stretchy, and transparent films. Results are shown in Tables 2, 3, 4. Examples of films are shown in FIG. 3A-3E.

TABLE 2

PLA/Polymer Films, 20-30 KDa

| Blend Components | % Composition | Film Characteristics |
|---|---|---|
| PLA | 100 | Thin films would not peel off the plate |
| PLA/Polymer | 70/30 | Slightly opaque and stretchy |
| PLA/Polymer | 85/15 | Transparent and very stretchy |
| PLA/Polymer | 90/10 | Transparent, soft, flexible and stretchy |
| PLA/Polymer | 95/5 | Transparent, soft, flexible, and stretchy |

TABLE 3

PLA/Polymer Films, 50 KDa

| Blend Components | % Composition | Film Characteristics |
|---|---|---|
| PLA/Polymer | 50/50* | Transparent, soft, and stretchy |
| PLA/Polymer | 50/50** | White tape-like film, soft, and flexible |
| PLA/Polymer | 85/15*** | Transparent, flexible, soft |

% solids: *5.0, 10.0, and *20.0

TABLE 4

PLA/Polymer Films, 100 KDa

| Blend Components | % Composition | Film Characteristics |
|---|---|---|
| PLA/Polymer | 85/15* | Transparent, flexible, soft |

*13% solids

Example 5

In Vitro Release Study

Conversion of the polymer to monomer, dimer, and trimer under post-ruminal conditions for nutritional applications was studied. An polymer sample (0.400 g, HMTBa homopolymer) was added to a flask containing 50 mL phosphate buffer and agitated at 39.0° C., 200 rpm for 24 h. Aliquots were taken at different times (0, 30, 60, 120, 270 min, and at 24 h) to follow monomer conversion by HPLC.

At pH 6.5 no change in polymer composition was observed by HPLC, whereas at pH 2.5 the composition was converted to monomer, dimer and trimer exclusively.

In conclusion in-vitro studies indicated that the polymer is hydrolyzed to monomer, dimer, and trimer at pH 2.5 which is essential for ruminant nutrition purposes to by pass rumen degradation at pH 6.5.

Example 6

In Vivo Efficacy Study in Chickens

Figure 4:
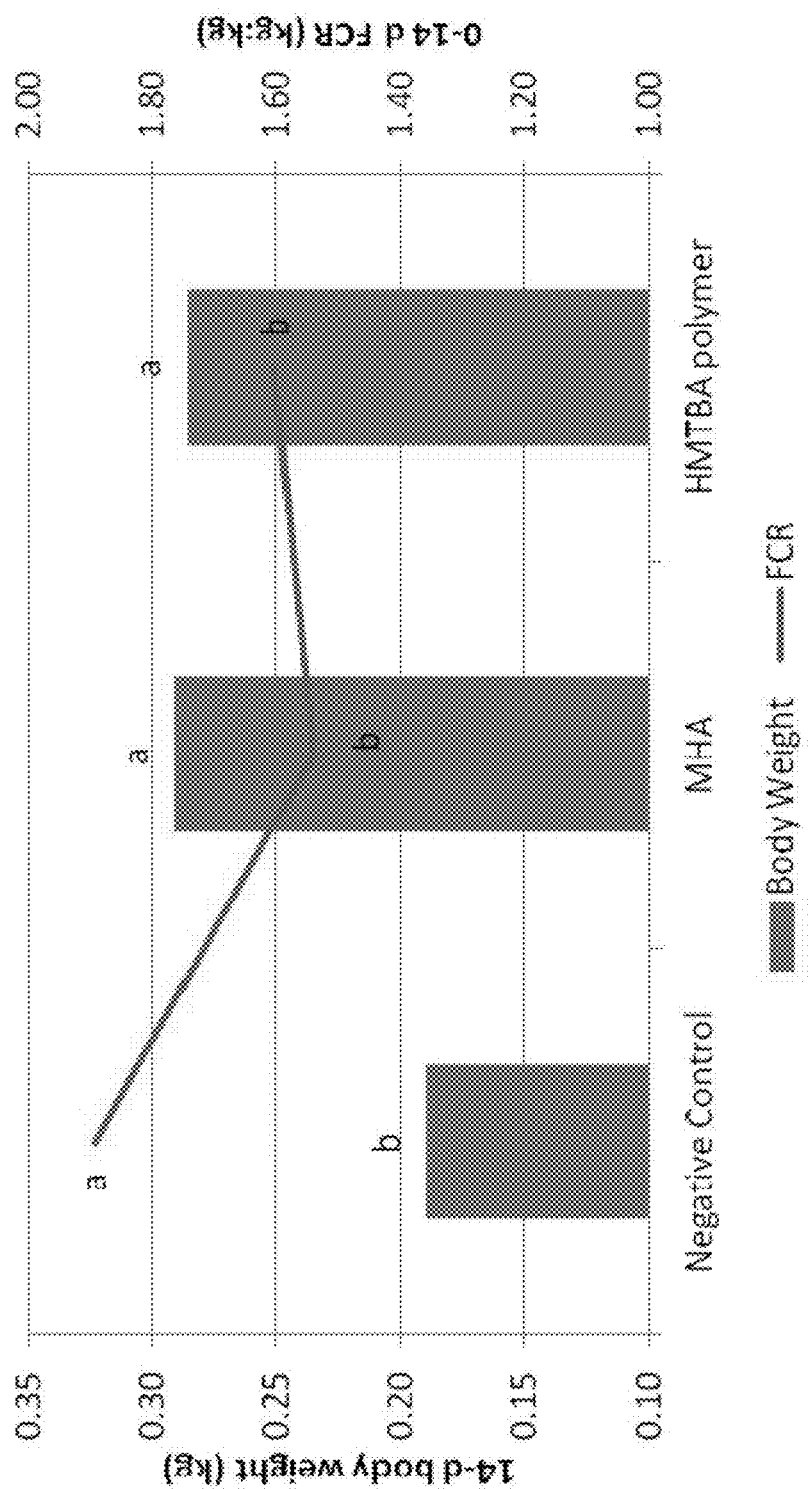
FIG. 4 shows a chart of the weight gain and feed conversion rate (FCR) for young broilers fed HMTBa calcium salt (MHA) and HMTBA homopolymer against a negative control with a diet deficient in methionine. Treatments within the same comparison without common superscripts differ significantly ($P<0.05$).

HMTBA homopolymer was compared to HMTBA calcium salt (MHA) in young broilers chicks as methionine source with a diet deficient in dietary methionine (0.26%) as negative control. A total of 108 Ross 708 male broilers were randomly assigned to 18 battery pens with 6 birds per pen. Six replicate pens were fed one of the 3 test diets from 0 to 14 days of age. HMTBA and MHA were added at equal molar basis to provide 0.15% added methionine. Growth performance parameters including body weight, feed conversion ratio (FCR), feed intake, and mortality, were measured and the body weight and FCR results are shown in FIG. 4. Supplementation of MHA significantly increased body weight, weight gain, performance index, and significantly improved FCR, which confirmed that the basal diet was deficient in methionine. Broilers fed HMTBA polymer had similar body weight, weight gain, FCR, feed intake, and performance index as those fed MHA, indicating HMTBA polymer was highly available to broilers as a methionine source and its bioavailability was not different from MHA.

What is claimed is:

1. A process for forming a homopolymer or copolymer having an average molecular weight above about 800 Da and a repeat unit comprising Formula (I), the process comprising contacting monomers comprising Formula (V):

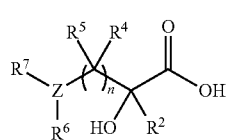

(V)

under dehydration conditions with an acid catalyst to form the polymer or copolymer having the repeat unit comprising Formula (I):

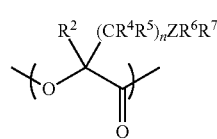

(I)

wherein,
$R^2$, $R^4$, and $R^5$ are independently chosen from hydrogen, hydrocarbyl, and substituted hydrocarbyl;
$R^6$ is chosen from hydrogen, hydrocarbyl, and substituted hydrocarbyl;
$R^7$ is optionally present, when present it is chosen from hydrogen, hydrocarbyl, and substituted hydrocarbyl;
Z is chosen from sulfur, sulfone, sulfoxide, and selenium; and
n is an integer $\geq 1$.

2. The process of claim 1, wherein the acid catalyst is stannous octoate.

3. The process of claim 1, wherein dehydration comprises azeotropic distillation.

4. The process of claim 1, where in the homopolymer or copolymer produced contains less than 2% of a free monomer.

5. The process of claim 1, where in the homopolymer or copolymer produced contains less than 1% of a free monomer.

6. The process of claim 1, where in the homopolymer or copolymer produced contains less than 0.5% of a free monomer.

7. The process of claim 1, wherein Z is sulfur, $R^6$ is methyl, n is 1, and $R^7$ is not present.

8. A process for preparing a homopolymer having an average molecular weight above about 800 Da the process comprising contacting monomers comprising Formula (V):

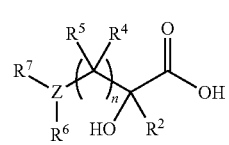

(V)

under dehydration conditions with an acid catalyst to form the polymer or copolymer having the repeat unit comprising Formula (I):

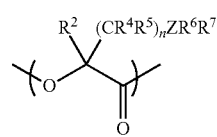

(I)

wherein,
$R^2$, $R^4$, and $R^5$ are hydrogen;
$R^6$ is chosen from hydrogen, hydrocarbyl, and substituted hydrocarbyl;
$R^7$ is not present;
Z is chosen from sulfur, sulfone, sulfoxide, and selenium; and
n is an integer $\geq 1$.

9. The process of claim 8, wherein the acid catalyst is stannous octoate.

10. The process of claim 8, wherein dehydration comprises azeotropic distillation.

11. The process of claim 8, where in the homopolymer or copolymer produced contains less than 2% of a free monomer.

12. The process of claim 8, where in the homopolymer or copolymer produced contains less than 1% of a free monomer.

13. The process of claim 8, where in the homopolymer or copolymer produced contains less than 0.5% of a free monomer.

14. The process of claim 8, wherein Z is sulfur and $R^6$ is methyl.

15. A process for preparing a homopolymer having an average molecular weight above about 800 Da the process comprising contacting monomers comprising Formula (V):

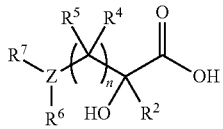

(V)

under dehydration conditions with stannous octoate to form the polymer or copolymer having the repeat unit comprising Formula (I):

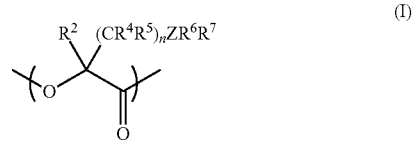

(I)

wherein, $R^2$, $R^4$, and $R^5$ are hydrogen;

$R^6$ is methyl;

$R^7$ is not present;

Z is sulfur; and n is 1.

16. The process of claim 15, wherein dehydration conditions comprise azeotropic distillation.

17. The process of claim 15, wherein stannous octoate is added after azeotropic distillation under nitrogen at a temperature of about 120° C. to about 150° C. for about 4 to about 5 hours.

* * * * *